United States Patent
Cho et al.

(10) Patent No.: US 7,335,766 B2
(45) Date of Patent: Feb. 26, 2008

(54) METHOD FOR PRODUCING A CHITOSAN CONTAINING SALT HAVING A FUNCTION OF LOWERING BLOOD PRESSURE

(75) Inventors: Gun Sik Cho, 101-1405 Dongbaek Apt., Sanjeong-dong, Mokpo Jeonnam 530-210 (KR); Gye Yeop Kim, Gwangju (KR); Kyung Sik Ham, Gwangju (KR); Hyun Jin Park, Seoul (KR); In Cheol Kim, Gwangju (KR)

(73) Assignee: Gun Sik Cho, Jeonnan (KR)

( * ) Notice: Subject to any disclaimer, the term of this patent is extended or adjusted under 35 U.S.C. 154(b) by 314 days.

(21) Appl. No.: 10/518,419

(22) PCT Filed: Feb. 27, 2004

(86) PCT No.: PCT/KR2004/000410

§ 371 (c)(1),
(2), (4) Date: Dec. 17, 2004

(87) PCT Pub. No.: WO2004/100681

PCT Pub. Date: Nov. 25, 2004

(65) Prior Publication Data

US 2005/0232999 A1    Oct. 20, 2005

(30) Foreign Application Priority Data

May 19, 2003 (KR) .................. 10-2003-0031616

(51) Int. Cl.
*C08B 37/08* (2006.01)
*C08B 37/00* (2006.01)
*A61K 31/722* (2006.01)

(52) U.S. Cl. ............. 536/55.3; 536/20; 536/18.7; 514/55; 424/489

(58) Field of Classification Search ........... 536/55.3, 536/20, 18.7; 514/55; 424/489
See application file for complete search history.

(56) References Cited

FOREIGN PATENT DOCUMENTS

| KR | 19950005196 A | 3/1995 |
|---|---|---|
| KR | 010000706 A | 5/2001 |
| KR | 20010103538 A | 11/2001 |

OTHER PUBLICATIONS

STN: abstract of Cho et al.; KR 2001000706 A, May 1, 2001 (Abstract sent).*

* cited by examiner

*Primary Examiner*—Shaojia Anna Jiang
*Assistant Examiner*—Michael C. Henry
(74) *Attorney, Agent, or Firm*—Steven J. Hultquist; Intellectual Property/Technology Law (57) ABSTRACT

The present invention relates to a method for producing a chitosancontaining salt having the function of lowering blood pressure. The method comprises the steps of: (a) dissolving an acid-soluble chitosan in organic acid, or dissolving a water-soluble chitosan derivative in water, to prepare a chitosan solution; (b) spraying the chitosan solution on salt particles to bind the chitosan to the salt particles; and (c) drying the chitosan-bound salt particles. According to the present invention, the chitosan or its derivative is bound to the salt particles by spraying or mixing such that the chitosan-containing salt can be produced without performing a recrystallizing step. Thus, the production cost of the chitosan-containing salt can be significantly decreased.

7 Claims, 6 Drawing Sheets

<Prior Art>

70% granule, 30% powder

<Present Invention>

90% granule, 10% powder ent content at significantly decreased costs.

METHOD FOR PRODUCING A CHITOSAN CONTAINING SALT HAVING A FUNCTION OF LOWERING BLOOD PRESSURE

TECHNICAL FIELD

The present invention relates to a method for producing a chitosan-containing salt having the function of lowering blood pressure, the method being characterized by binding chitosan or its derivative to salt particles. More particularly, the present invention relates to a method for producing a chitosan-containing salt, which comprises dissolving an acid-soluble chitosan in organic acid or dissolving a water-soluble chitosan derivative in water, to prepare a chitosan solution, spraying the chitosan solution on salt particles to bind the chitosan or its derivative to the salt particles, and drying and finely grinding the chitosan-bound salt particles.

BACKGROUND ART

Patients with cardiac vascular diseases, such as hypertension, or adult diseases, hard to cure, such as diabetes and renal failure, are recommended to limit salt or to take a small amount of salt. As salt which may be given to a patient with hypertension, there is now only salt whose sodium chloride (NaCl) content is reduced by adding potassium chloride (KCl). Even a functional salts, there are only garlic salt and green tea salt whose clinical results have not yet been found.

Hypertension is mainly described by a physiochemical mechanism caused by renin-angiotensin, and substances capable of inhibiting the activity of angiotensin converting enzyme (ACE) are currently of high concern for direct inhibition of hypertension. In addition to producing dipeptide, ACE is presumed to show an enzyme reaction mechanism similar to pancreatic carboxypeptidase A. On the basis of this presumption, chemically synthesized ACE inhibitor, such as captopril and enarapril, are used as antihypertensive agents. However, since such chemical products have many problems, such as safety, side effects, and the like, the searching of peptide-based ACE inhibitory substance from various natural substances is being continued.

Steady intake of food containing the ACE inhibitory substance will help the prevention or alleviation of hypertension. Chitosan is one of the biopolymer substances, prepared by deacetylating chitin which a kind of animal polysaccharides, present in the shell of shellfish, such as crabs or lobsters, and is known as the ACE inhibitory substance. Chitosan is a polysaccharide linked by β-1,4-bond of D-glucosamine, and includes α-chitosan derived from shellfishes, β-chitosan from molluscs, and γ-chitosan from microbial strains.

Strictly speaking, chitosan can be defined as a chitin derivative, and acid-soluble chitosan is generally called "chitosan". Examples of water-soluble chitosan include CM-chitosan (carboxymethyl-chitosan which carboxymethyl group is given by a chemical numerical formula), S-chitosan (oligosaccharide-chitosan), SCM-chitosan (N-sulfide derivative of N-deacetylated CM chitin), HP-chitosan (hydroxyl-propyl-chitosan), etc. Also, according to molecular weight, monosaccharide is called "glucosamine", a complex of 2~9 monosaccharides is called "oligochitosan", and a complex of more than 10 monosaccharides is called "chitosan".

To make patients with hypertension or diabetes, avoid excessive intake of salt with low purity, such as a mixture of potassium chloride (50%) and sodium chloride (50%), has appeared, but its effect on hypertension has not been proved yet.

Meanwhile, Korean patent publication 95/5196A disclosed a liquid salt seasoning comprising a mixture of salt and chitosan. However, this patent application has no mention of a blood pressure lowering efficacy, and also has problems that it is not easy to mix seasoning liquid with 1~3% of chitosan, since it is difficult for chitosan generally being participated in alkaline water due to having an isoelectric point of pH 6.5, to be dissolved, and chitosan with a high-molecular weight is in a gel form even in acetic acid due to its high viscosity.

Furthermore, methods for producing chitosan salt are known, in which chitosan dissolved in organic acid is mixed with salt solution, and the mixture is subjected to stirring, evaporating, drying and crystallizing steps (Korean patent publication KR 01/00706A and KR 01/103538A). However, KR 01/103538A has no mention of the blood pressure lowering efficacy of the chitosan salt. KR 01/00706A suggests the blood pressure lowering efficacy of the chitosan salt, but has a problem that it requires the recrystallizing step so that production process is complex and a great increase in production costs is caused upon the mass production of the chitosan salt.

DISCLOSURE OF INVENTION

The present inventors have conducted many researches to solve the above-mentioned problems occurring in the prior art, and consequently, found that when a solution of chitosan is sprayed on salt particles to bind the chitosan to the salt particles, chitosan-containing salt having a blood pressure lowering function can be economically produced without performing a recrystallization process. On the basis of this discovery, the present invention was perfected.

Accordingly, an object of the present invention is to provide a method for producing chitosan-containing salt, which can produce the chitosan-containing salt by a simplified process at significantly decreased costs.

To achieve the above object, the present invention provides a method for producing a chitosan-containing salt having the function of lowering blood pressure, which comprises the steps of: (a) dissolving an acid-soluble chitosan in organic acid, or dissolving a water-soluble chitosan derivative in water, to prepare a chitosan solution; (b) spraying the chitosan solution on salt particles to bind the chitosan to the salt particles; and (c) drying the chitosan-bound salt particles.

The chitosan used in the step (a) of the inventive method is preferably α-chitosan or β-chitosan. Also, the chitosan or its derivative used in the step (a) has preferably a molecular weight of 10~100 kDa. The content of the chitosan or its derivative in the chitosan-containing salt is preferably 1.5~5%.

Moreover, the organic acid used in the step (a) preferably is lactic acid, acetic acid or ascorbic acid, and the salt used in the step (b) is preferably natural sea salt, refined salt or rock salt, which has the size of 10~50 mesh.

In a preferred embodiment of the present invention, natural sea salt produced in Korea is processed. Meanwhile, low-molecular weight chitosan is dissolved in an aqueous solution of organic acid (lactic acid, acetic acid or ascorbic acid), or a chitosan derivative is dissolved in water, to prepare a chitosan solution.

The chitosan solution is bound to the processed salt particles by a spraying or mixing process. The chitosan-bound salt particles are dried to produce a chitosan-containing salt. As the chitosan used in this embodiment, α-, β- or γ-chitosan may be used, but the α-chitosan which is produced at large amounts and at a low cost is suitable.

The molecular weight of the chitosan is not specially limited. However, a chitosan having a molecular weight of 0.5~500 kDa is preferred since it shows good binding force to the chlorine ion of salt. A chitosan having a molecular weight of 10~100 kDa is more preferred since it is soft and has a good taste after intake without lowering the properties of salt. The chitosan content in the chitosan-containing salts is preferably 0.05~5%, and more preferably 1.5~5%. If the chitosan content is less than 1.5%, the blood pressure-lowering function of the chitosan-containing salt will be insufficient, and if the chitosan content is more than 5%, the taste of the chitosan-containing salt will be lessened due to an acrid taste of the chitosan. In addition, both the water-soluble chitosan and the acid-soluble chitosan may be used in the present invention.

DETAILED DESCRIPTION OF THE INVENTION

The present invention will hereinafter be described in further detail by examples. It will however be obvious to a person skilled in the art that the examples are given only to illustrate the producing method and blood pressure lowering efficacy of chitosan-containing salt, and the scope of the present invention is not limited to or by the examples.

EXAMPLE 1

Production of Chitosan-Containing Salt

Low-molecular weight chitosan with a molecular weight of 50 kDa (deacetylation degree of 90%) was dissolved in an aqueous solution of 5% lactic acid, to prepare a solution of 10 wt % chitosan. 10 kg natural sea salt produced in Korea was processed into particles having a size of 15 mesh, and then 1, 2 and 3 liter of 10 wt % chitosan solution was sprayed on the salt particles respectively so that the chitosan was coated on, or bound to the salt particles. The chitosan-coated or -bound salt particles were dried to produce chitosan-containing salts having chitosan contents of 1%, 2% and 3%, respectively.

According to the same method as described above, 2% chitosan-containing salts were prepared using chitosan with molecular weights of 20, 40 and 100 kDa, respectively.

EXAMPLE 2

ACE Inhibitory Effect of Chitosan-Containing Salt

To examine the ACE inhibitory effect of the chitosan-containing salt produced in Example 1 above, 100 μl of 2% chitosan-containing salt dissolved in distilled water was added to 250 μl of a reaction solution. The mixed solution was left alone for 5 minutes at 37° C., to which 50 μl of ACE was added and allowed to react for 30 minutes. Then, the reaction was terminated by adding 250 μl of 1N HCl. The reaction product was mixed with 1.5 ml of ethyl acetate for 15 seconds and centrifuged. 1 ml of the supernatant was taken and dried in a speed bag with the removal of the ethyl acetate. Then, the remaining material was dissolved in 1 ml of distilled water and measured for the absorbance at 228 nm. From the measured absorbance, ACE inhibitory activity was calculated according to the following equation:

$$\text{ACE inhibitory activity}(\%) = (1 - A/B) \times 100;$$

where A is the absorbance of a group added with the sample, and B is the absorbance of a group without addition of the sample.

Figure 1:
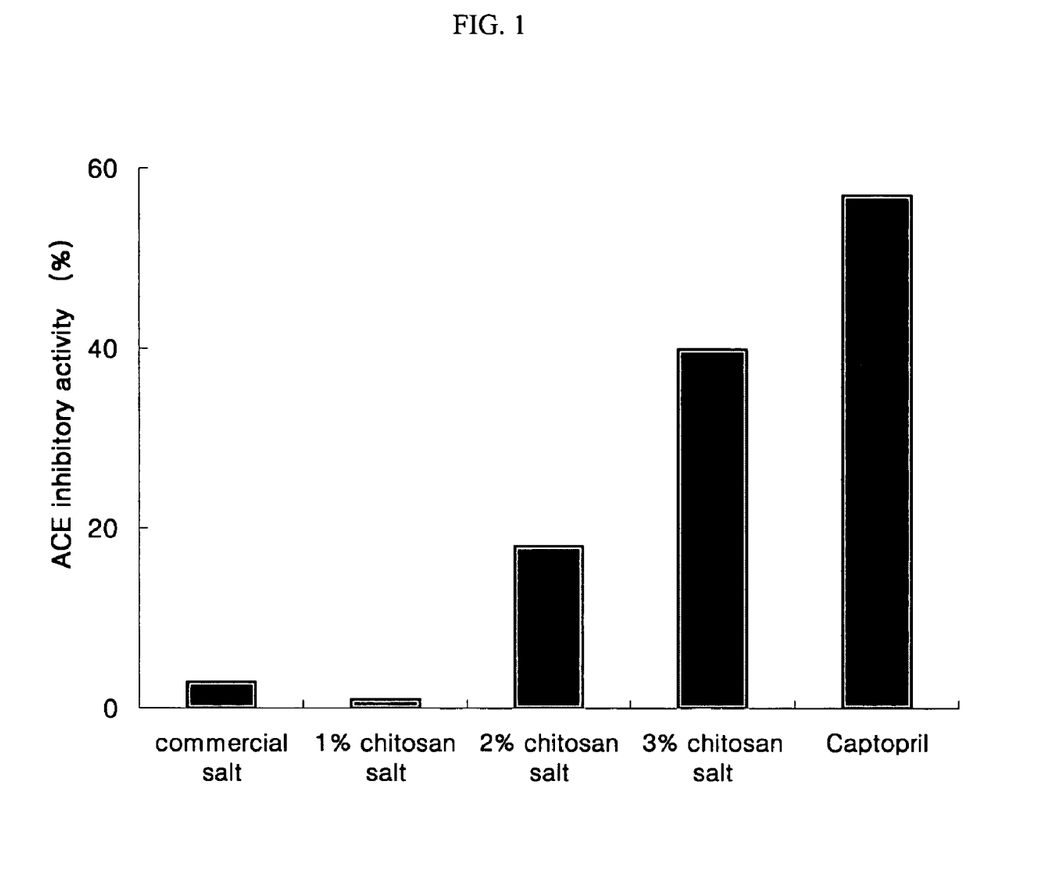
FIG. 1 is a graphic diagram showing the ACE inhibitory activity of a chitosan-containing salt.

The ACE inhibitory activities of commercial salt and chitosan-containing salt were examined (see FIG. 1). As shown in FIG. 1, captopril (control group), a chemically synthesized inhibitor, showed 57%, which is the highest ACE inhibitory activity, the salt containing 3% chitosan showed an ACE inhibitory activity of 39.1%, and the commercial salt had little ACE inhibitory activity. It could be found that the commercial salt acted to increase the ACE activity whereas the chitosan-containing salt had a very excellent ACE inhibitory effect.

Figure 2:
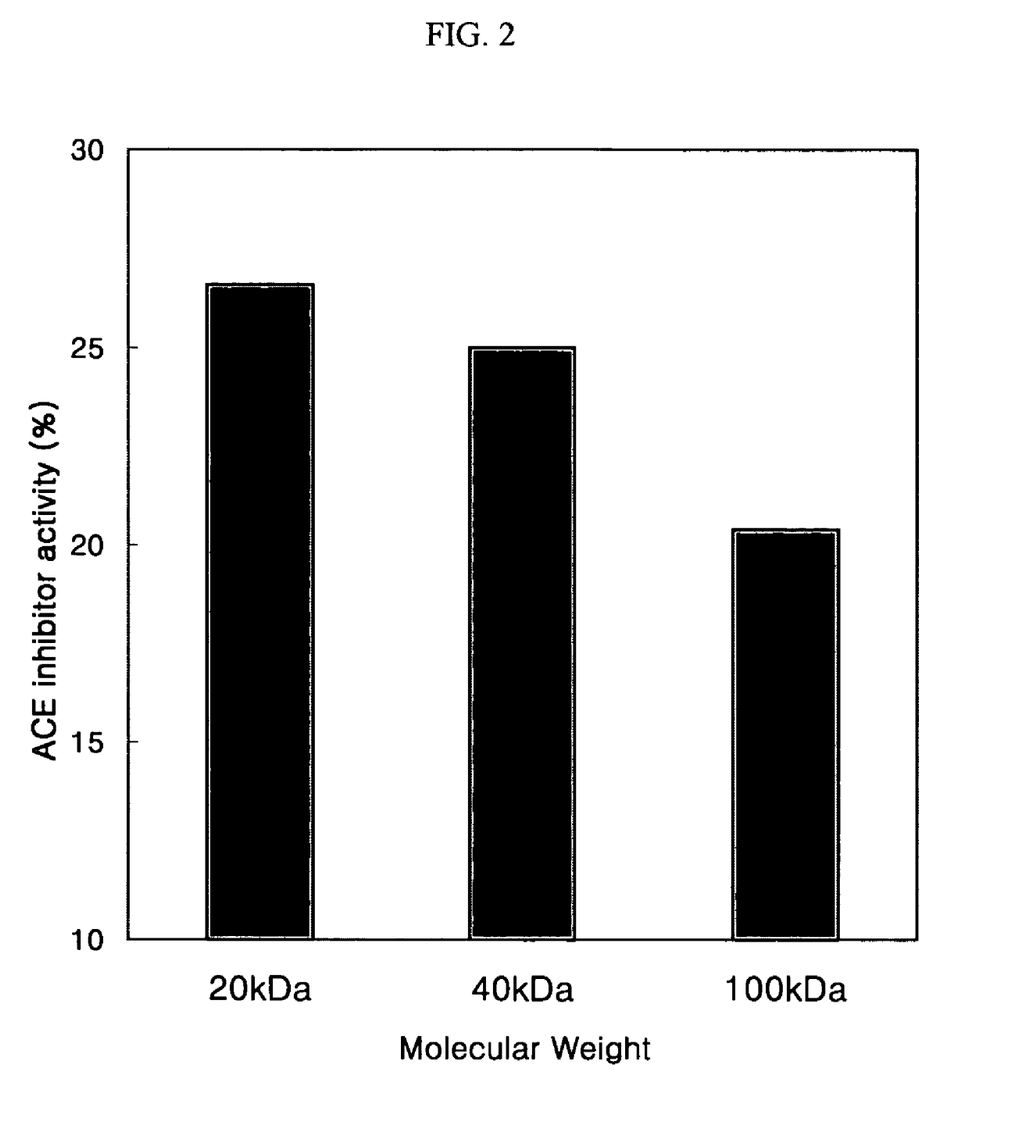
FIG. 2 is a graphic diagram showing the ACE inhibitory activity of a chitosan-containing salt according to the molecular weight of chitosan.

Also, the ACE inhibitory activity of the chitosan-containing salt was examined while maintaining the chitosan content at a level of 2% and changing the chitosan molecular weight from 20 kDa to 40 and 100 kDa (see FIG. 2). As shown in FIG. 2, the chitosan-containing salt showed 27%, which is the highest ACE inhibitory activity at a molecular weight of 20 kDa, and the ACE inhibitory activity of the chitosan-containing salt was somewhat decreased with an increase of the molecular weight of the chitosan.

EXAMPLE 3

Measurement of Blood Pressure of Rats According to Administration of Chitosan-Containing Salt 16-week-old rats were divided into a control group fed with no salt feed, a group fed with 3% commercial salt feed, and a group fed with 3% chitosan salt feed, each group consisted of six rats. While the rats were bred for 5 weeks, the systolic pressure at the tail of the rats was measured once every week. One kg of feed to the experimental rats was composed of 544.9 g of corn, 20 g of soybean oil, 0.1 g of cholin chloride, 20 g of a vitamin mixture, 240 g of casein, 145 g of sugar and 30 g of salt. The blood pressure of the rats was measured with an RTBP 2000 single-channel system (World Precision Instruments), and the concentrations of sodium, chlorine and cholesterol in blood were measured with an UV spectrophotometer (Hitachi 7060).

Figure 3:
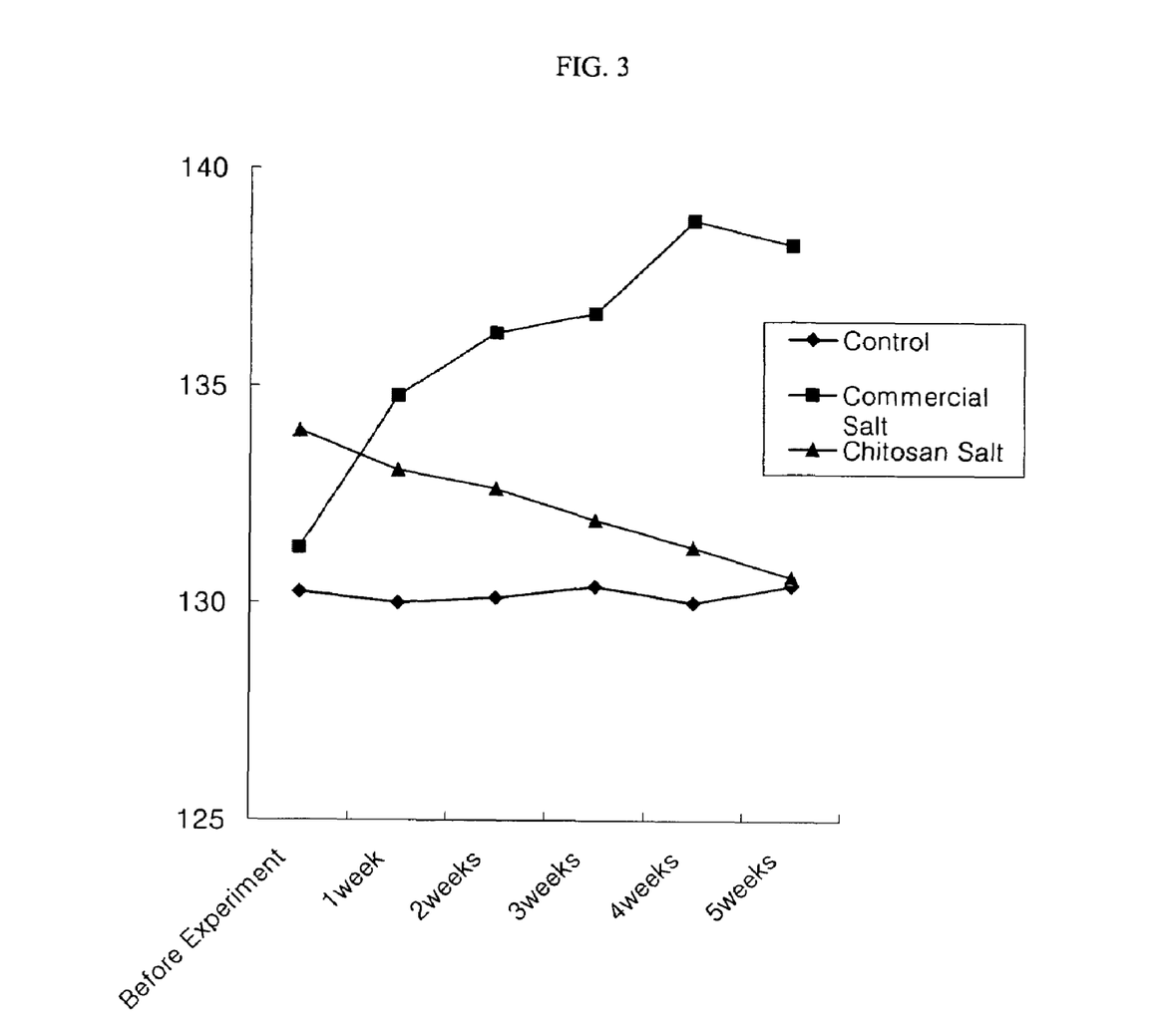
FIG. 3 is a graphic diagram showing the result of measurement of blood pressure of rats according to the administration of a chitosan-containing salt.

In the results of measurement, the rats fed with 3% commercial salt feed showed about a 7 mmHg increase in blood pressure as compared to that before the experiment, whereas the rats fed with 3% chitosan salt feed showed about a 3 mmHg decrease in blood pressure (see FIG. 3). This result of blood pressure reduction is presumed to be caused by the reduction of chlorine ion concentration in blood. This suggests that the chitosan acts to excrete an excess of the chlorine ions of salt out of the body.

Figure 4:
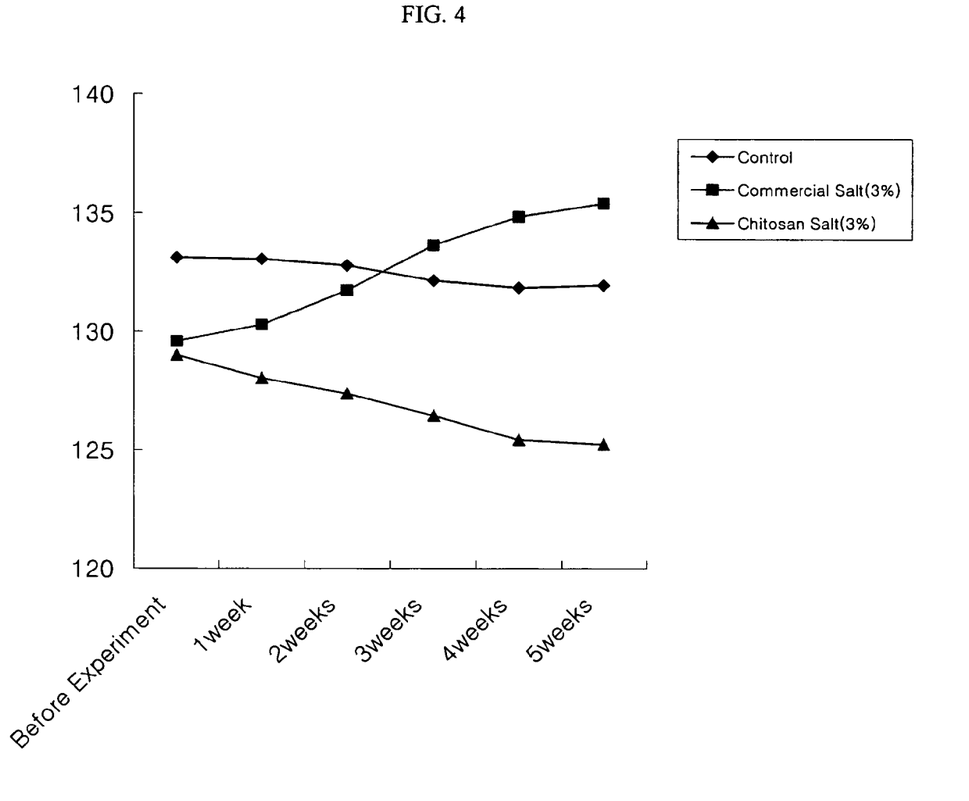
FIG. 4 is a graphic diagram showing the correlation between salt and blood pressure according to the administration of chitosan-containing salt, when having had the rats exercise for two hours a day during breeding.

Meanwhile, when the rats were allowed to move for two hours a day during breeding, the rats fed with 3% commercial salt feed showed about a 6 mmHg increase in blood pressure, whereas the rats fed with 3% chitosan salt feed showed about a 4 mmHg decrease in blood pressure (see FIG. 4).

Furthermore, blood was collected from the rats at one month after the start of breeding, and analyzed for its Na and Cl ion concentrations. In the analysis results, chlorine concentration, cholesterol and neutral lipid in the control group fed with no salt feed have became lowered as compared to those before the experiment, but sodium and chlorine concentrations in the rats fed with 3% commercial salt feed has became increased as compared to those before the experiment. Meanwhile, it could be found that chlorine concentration and cholesterol in the rats fed with 3% chitosan salt feed has became lower than those in the rats fed with 3% commercial salt feed (see Table 1).

control group was continuously decreased, whereas blood pressure in the rats treated with commercial salt was slowly increased and after one month, an average of 5 mmHg increased to reach a risk level. However, blood pressure in the rat group fed with the chitosan salt was lowered incredibly.

Moreover, the measurement of Cl ion concentration in blood was performed. The results showed that the Cl ion concentration was 102.8 mM in the animal group administered with 3% commercial salt feed, but 97.7 mM in the group administered with 3% chitosan salt feed, which indicates a reduction of 5.1 mM in Cl ion concentration as compared to the commercial salt group. Such results suggest that the Cl ion is a main factor causing an increase in blood pressure.

EXAMPLE 5

Economic Efficiency of Inventive Method for Producing Chitosan-Containing Salt

Figure 6:
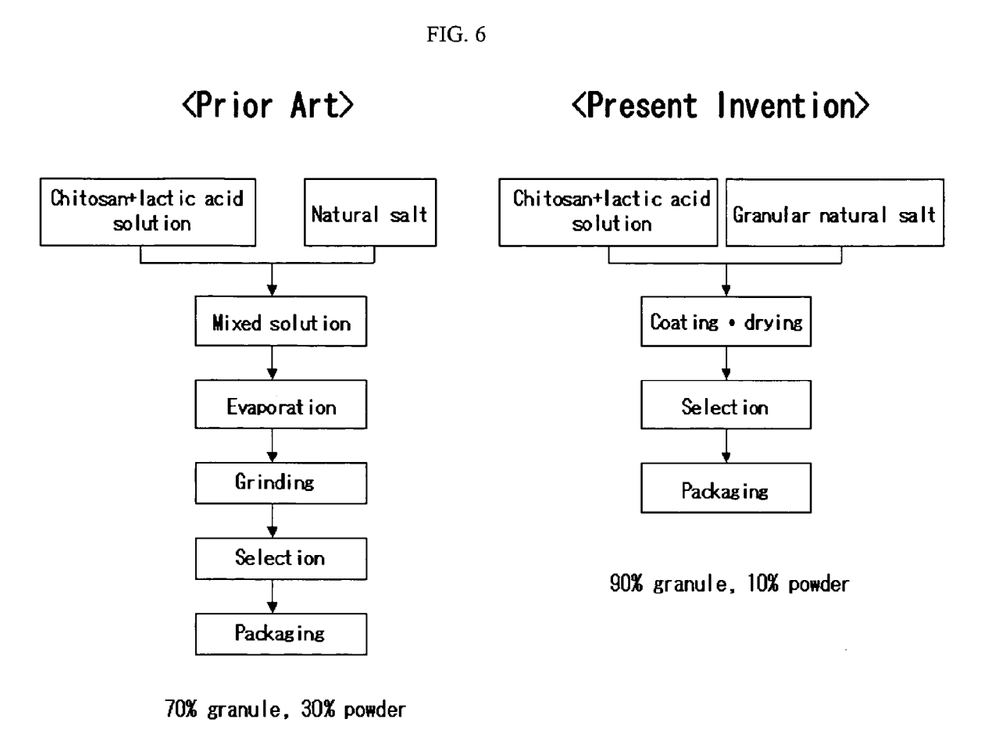
FIG. 6 shows the comparison between methods for producing chitosan-containing salt according to the present invention and the prior art.

In a method for producing chitosan-containing salt according to the prior art, chitosan, lactic acid and natural sea salt are mixed with each other to prepare a mixture solution. The mixture solution is dried by evaporation, and then subjected to grinding, screening and packaging steps. In contrast to this, in the producing method of the present invention, an aqueous solution of chitosan and lactic acid is coated on or bound to granular natural sea salt by spraying, and then subjected to screening and packaging steps. Thus, the inventive method for chitosan-containing salt requires no tank facilities for the preparation of the mixture solution and

TABLE 1

Changes of Na and Cl ion concentrations, cholesterol and neutral lipid according to intake of chitosan-containing salt (TC: cholesterol; and TG: neutral lipid)

| Contents | Before the experiment Control | One month after the start of breeding | | |
|---|---|---|---|---|
| | | Control (salt 0%) | 3% chitosan-containing salt feed | 3% commercial salt feed |
| Na(mM) | 141.8 | 141.8 | 148.6 | 149.9 |
| Cl(mM) | 99.5 | 96.2 | 97.7 | 102.8 |
| TC | 112.3 | 92.6 | 105.5 | 113.8 |
| TG | 27.15 | 24.1 | 32.3 | 28.5 |

EXAMPLE 4

Figure 5:
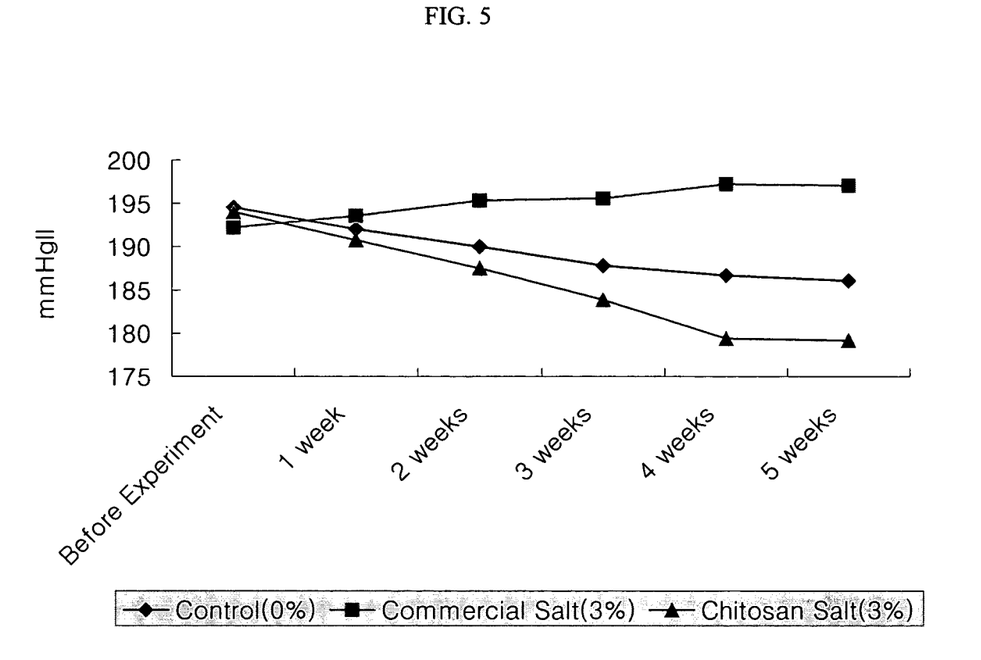
FIG. 5 is a graphic diagram showing the result of measurement of blood pressure according to the intake of chitosan-containing salt of hypertension-induced rats.

Blood Pressure Lowering Effect of Chitosan-Containing Salt in Hypertension-Induced Rats The same experiment as in Example 3 was performed on hypertension-induced rats (see FIG. 5). As shown in FIG. 5, the experiment results showed that blood pressure in the enables the recrystallizing and grinding steps to be eliminated (see FIG. 6).

Energy costs required for the mass production of the chitosan-containing salt were compared between the prior art (Korean patent publication 01/00706A) and the inventive method. As shown in Table 2, energy cost required to produce 300 kg of chitosan-containing salt by the prior art (KR 01/00706) was about 33,175 won in Korean currency.

TABLE 2

Comparison of energy costs required in producing 300 kg of chitosan-containing salt according to prior art method and inventive method

| Contents | Prior art method | This inventive method |
| --- | --- | --- |
| Raw materials | (chitosan + lactic acid) solution 1000 L (chitosan 3 wt %, lactic acid 1.5 wt %) + natural sea salt 270 kg | (chitosan + lactic acid) solution 100 L (chitosan 10 wt %, lactic acid 5 wt %) + granulated natural sea salt 290 kg |
| Amount of water to be evaporated | 955 L | 85 L |
| Consuming heat capacity | 955 L × 597.5(enthalpy of water at 0° C.) = 570,612.5 kcal | 85 L × 597.5(enthalpy of water at 0° C.) = 50,787.5 kcal |
| Consuming electric energy | 570,612.5 kcal ÷ 860 kcal/kw = 663.5 kw | 50,787.5 kcal ÷ 860 kcal/kw = 59.1 kw |
| Energy cost | 663.5 kw × 50 won/kw = 33,175 won | 60 kw × 50 won/kw = 2,955 won |

Meanwhile, according to the inventive method, 100 liter of aqueous solution containing 10% chitosan and 5% lactic acid was prepared, coated on or bound to 290 kg of granular natural sea salt by spraying, and then subjected to drying and screening steps. In which case, the amount of water to be evaporated was 85 liters, and a heat capacity of 50,787.5 kcal was consumed, which indicates an electric energy of 59.1 kw. Thus, energy cost in producing 300 kg of the chitosan-containing salt according to the inventive method was 2,995 won in Korean currency, which is at least 11 times lower than that of the prior art.

INDUSTRIAL APPLICABILITY

As described above, the inventive method for producing the chitosan-containing salt is simpler than the prior art method. Moreover, it can be advantageously applied to the mass production of the chitosan-containing salt and enables production of the chitosan-containing salt having uniform quality.

According to the present invention; the chitosan or its derivative is bound to the salt particles by spraying or mixing such that the chitosan-containing salt can be produced without performing a recrystallizing step. Thus, the production cost of the chitosan-containing salt can be significantly decreased.

What is claimed is:

1. A method for producing a chitosan-containing salt having the function of lowering blood pressure, which comprises the steps of:

(a) dissolving an acid-soluble chitosan in organic acid, or dissolving a water-soluble chitosan in water, to prepare a chitosan solution;

(b) spraying the chitosan solution on salt particles to bind the chitosan to the salt particles; and (c) drying the chitosan-bound salt particles.

2. The method for producing a chitosan-containing salt according to claim 1, wherein the chitosan is α-chitosan or β-chitosan.

3. The method for producing a chitosan-containing salt according to claim 1, wherein the chitosan has a molecular weight in a range of from 10 to 100 kDa.

4. The method for producing a chitosan-containing salt according to claim 1, wherein the organic acid is lactic acid, acetic acid or ascorbic acid.

5. The method for producing a chitosan-containing salt according to claim 1, wherein the salt is natural sea salt, refined salt or rock salt.

6. The method for producing a chitosan-containing salt according to claim 1, wherein the salt has the size in a range of from 10 to 50 mesh.

7. The method for producing a chitosan-containing salt according to any one claim among claims 1 to 6, wherein the content of the chitosan in the chitosan-containing salt is from 1.5 to 5%.

* * * * *